United States Patent [19]

Kelly

[11] 4,264,508
[45] Apr. 28, 1981

[54] TRICYCLIC LACTONE INTERMEDIATES FOR PREPARING PROSTAGLANDINS

[75] Inventor: Robert C. Kelly, Kalamazoo, Mich.

[73] Assignee: The Upjohn Company, Kalamazoo, Mich.

[21] Appl. No.: 96,805

[22] Filed: Nov. 23, 1979

Related U.S. Application Data

[62] Division of Ser. No. 654,109, Feb. 2, 1976, abandoned.

[51] Int. Cl.³ ............................................. C07D 307/93
[52] U.S. Cl. .......................... 260/343.21; 260/343.3 P
[58] Field of Search ...................... 260/343.3 P, 343.21

[56] References Cited

U.S. PATENT DOCUMENTS 3,873,571  3/1975  Kelly ............................. 260/343.3 P

*Primary Examiner*—Henry R. Jiles
*Assistant Examiner*—Jane T. Fan
*Attorney, Agent, or Firm*—Robert A. Armitage

[57] ABSTRACT

Process for preparing bicyclic lactone acrylic aldehydes and ketones of the formula

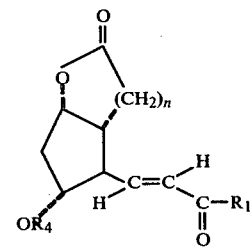

wherein "n" is one or 2, wherein $R_1$ is hydrogen, methyl, or ethyl, and wherein $R_4$ is hydrogen or a blocking group; and those aldehydes, ketones, and intermediates prepared therein. The aldehydes and ketones are useful intermediates in preparing prostaglandins and analogs having pharmacological utility.

1 Claim, No Drawings

TRICYCLIC LACTONE INTERMEDIATES FOR PREPARING PROSTAGLANDINS

The present application is a divisional application of Ser. No. 654,109, filed Feb. 2, 1976, now abandoned. U.S. Ser. No. 096,806, filed Nov. 23, 1979, is also a divisional application of Ser. No. 654,109.

The present invention relates to prostaglandin analogs, for which the essential material constituting disclosure therefor is incorporated by reference here from U.S. Ser. No. 096,806.

I claim:

1. A compound of the formula

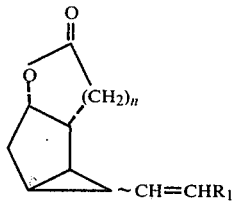

wherein n is one or 2, $R_1$ is hydrogen, and $\sim$ indicates attachment of $-CH=CHR_1$ to the cyclopropane ring in exo or endo configuration.

* * * * *

UNITED STATES PATENT OFFICE
CERTIFICATE OF CORRECTION

Patent No. 4,264,508          Dated 28 April 1981

Inventor(s) Robert C. Kelly

It is certified that error appears in the above-identified patent and that said Letters Patent are hereby corrected as shown below:

Column 1, line 7, "U.S. Ser. No. 096,806, filed Nov. 23, 1979," should read -- U.S. Ser. No. 096,806, filed Nov. 23, 1979, now U.S. Pat. 4,235,779, --; lines 11-12, "is incorporated by reference here from U.S. Ser. No. 096,806" should read -- is incorporated by reference here from U.S. Pat. 4,235,779 --.

*Signed and Sealed this*

*Twenty-eighth* Day of *July 1981*

[SEAL]

*Attest:*

*Attesting Officer*

GERALD J. MOSSINGHOFF

*Commissioner of Patents and Trademarks*